United States Patent [19]

Stults et al.

[11] Patent Number: 5,101,006
[45] Date of Patent: Mar. 31, 1992

[54] POLYIMIDES AND COPOLYIMIDES BASED ON HALO-OXYDIPHTHALIC ANHYDRIDES

[75] Inventors: Jeffrey S. Stults; Willis T. Schwartz, both of Grand Island, N.Y.

[73] Assignee: Occidental Chemical Corporation, Niagara Falls, N.Y.

[21] Appl. No.: 674,802

[22] Filed: Mar. 25, 1991

Related U.S. Application Data

[60] Continuation-in-part of Ser. No. 492,196, Mar. 13, 1990, Pat. No. 5,003,086, which is a division of Ser. No. 352,070, May 15, 1989, Pat. No. 3,943,642.

[51] Int. Cl.$^5$ ............... C08G 63/00; C08G 69/26; C08G 8/02; C07D 307/89
[52] U.S. Cl. .................. 528/188; 528/125; 528/126; 528/128; 528/170; 528/173; 528/174; 528/175; 528/220; 528/229; 528/329.1; 528/310; 528/350; 528/353; 549/241
[58] Field of Search ............ 528/125, 126, 128, 170, 528/175, 173, 174, 176, 188, 220, 229, 329.1, 310, 350, 353

[56] References Cited

U.S. PATENT DOCUMENTS

| | | | |
|---|---|---|---|
| 3,879,428 | 4/1975 | Heath et al. | 549/241 |
| 4,863,640 | 9/1989 | Scola | 549/241 |
| 5,003,031 | 3/1991 | Schwartz et al. | 528/125 |
| 5,003,086 | 3/1991 | Stults et al. | 549/241 |
| 5,021,168 | 6/1991 | Molinaro et al. | 549/241 |

*Primary Examiner*—John Kight, III
*Assistant Examiner*—P. Hampton-Hightower
*Attorney, Agent, or Firm*—James F. Tao; Arthur S. Cookfair

[57] ABSTRACT

Novel halogenated polyimides and co-polyimides comprise recurring imide structural units of the formula

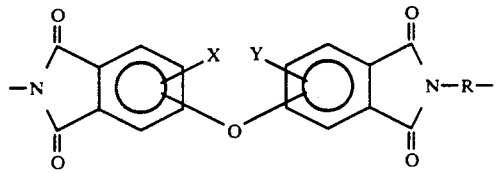

where X is F, Cl, Br or I; Y is H, F, Cl, Br or I; and R is a divalent organic radical.

8 Claims, No Drawings

POLYIMIDES AND COPOLYIMIDES BASED ON HALO-OXYDIPHTHALIC ANHYDRIDES

REFERENCE TO PRIOR APPLICATION

This is a continuation-in-part of Application Ser. No. 07/492,196, filed Mar. 13, 1990, now U.S. Pat. No. 5,003,086 which is a divisional of Application Ser. No. 07/352,070, filed May 15, 1989, now U.S. Pat. No. 3,943,642.

BACKGROUND OF THE INVENTION

This invention relates to polyimides which are prepared from halogenated oxydiphthalic anhydrides. Polyimides are used for various applications including films, coatings, and molded articles. Polyimides are generally characterized by excellent physical properties, such as high heat resistance, high impact strength and wear resistance, and the like. Polyimides are commonly prepared by polycondensation of a dianhydride and a diamine. The properties of polyimides can be varied depending on the specific dianhydride and diamine employed.

A variety of dianhydrides are shown in the literature as monomers in the preparation of polyimides.

U.S. Pat. No. 4,697,023 discloses the preparation of oxydiphthalic anhydrides and suggest their use in the preparation of polyimides. The oxydiphthalic anhydrides are prepared by the reaction of a halophthalic anhydride with water and an alkali metal compound such as KF, CsF, Or $K_2CO_3$ in the presence of a polar aprotic solvent.

Kolesnikov, G.S. et al, *Vysokomol. Soyed*, A9, 612–18 (1967); Marvel, C.S. et al, *J. Am. Chem. Soc.*, 80, 1197 (1958); and Latrova, Z.N. et al, *Volokna Sin. Polim.*, 15–24 (1970) disclose the preparation of oxydiphthalic acids and anhydrides by the oxidation of tetramethyldiphenyl ethers.

German Patent No. 2,416,594 (1975) discloses the preparation of oxydiphthalic anhydride by coupling of 3-nitrophthalic anhydride in the presence of metal nitrites such as sodium nitride.

U.S. Pat. No. 3,879,428 to Heath et al discloses the preparation of various aromatic bis(ether anhydrides) by reaction of nitrophthalimide with an alkali diphenoxide followed by hydrolysis to yield the diether anhydride.

Scola and Vontell (ChemTech, Feb. 1989, p 112) disclose the preparation of various polyimides, including fluorine-containing polyimides, based on fluorine-containing dianhydrides and/or diamines.

It will be generally appreciated by those skilled in the art that a need exists for a broader selection of polyimides based on the various properties needed for applications in the electrical, electronics, automotive, aerospace, and packaging industries. The polyimides of this invention are based on the use of novel halogenated oxydiphthalic anhydrides, optionally in combination with other anhydrides.

SUMMARY OF THE INVENTION

In accordance with the present invention, there is provided a novel class of polyimides and copolyimides comprising recurring imide structural units of the formula:

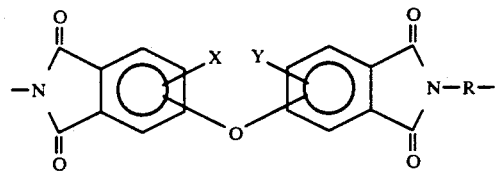

where X is F, Cl, Br, or I; Y is H, F, Cl, Br, or I; and R is a divalent organic radical.

DETAILED DESCRIPTION OF THE INVENTION

The present polyimides are prepared by condensation polymerization of essentially equimolar amounts of at least one dianhydride reactant comprising a halogenated oxydiphthalic anhydride of the formula

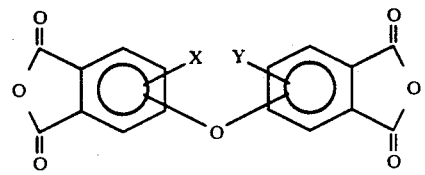

Where X is F, Cl, Br, or I and Y is H, F, Cl, Br, or I and at least one diamine reactant of the formula $NH_2RNH_2$ where R is a divalent organic radical selected from the group consisting of (a) aromatic hydrocarbon radicals having from 6 to about 20 carbon atoms and halogenated derivatives thereof, (b) alkylene radicals and cycloalkylene radicals having from 2 to about 20 carbon atoms, $C_{(2-8)}$ alkylene terminated polydiorganosiloxanes, and (c) divalent radicals included within the formula

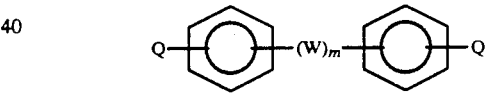

where Q is S, $SO_2$, O, or a direct bond; m is 0 or 1; and W is a member selected from the class consisting of divalent radicals of the formulas,

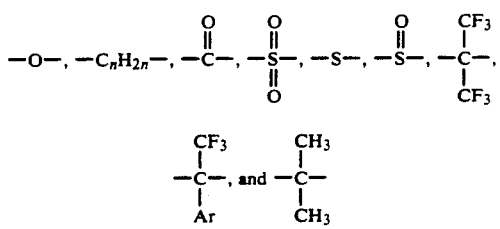

where n is a whole number from 1 to 5, and Ar is an aromatic hydrocarbon or halogen or halomethyl substituted aromatic hydrocarbon of 6 to 20 carbon atoms.

Among the diamines which are suitable for use in the present invention are:
Oxydianiline
Methylene dianiline
Oxy-4,4'-bis(2-trifluoromethylbenzamine)
Thio-4,4'-bis(2-trifluoromethylbenzamine)
Sulfonyl-4,4'-bis(2-trifluoromethylbenzamine)
Sulfoxyl-4,4'-bis(2-trifluoromethylbenzamine)

Oxy-4,4'-bis(3-trifluoromethylbenzamine)
Thio-4,4'-bis(3-trifluoromethylbenzamine)
Phenylenediamines
Diaminodiphenyl sulfone
Diaminobenzophenone
Diaminodiphenyl sulfide
Diaminobiphenyl
Diaminotoluene
Dimethylbenzidine
Mixtures of diamines may be employed.

A small amount of a mono-anhydride or a monoamine may be added to act as a chain stopper, to limit molecular weight. Furthermore, a small amount of a mono-anhydride or mono-amine containing additional reactive sites may be added to provide reactive endcaps for further reactions such as cross-linking or co-polymerization with other polymer structures.

The halogenated oxydiphthalic anhydrides employed in the preparation of the polyimides of this invention may be prepared by reacting a dihalophthalic anhydride of the

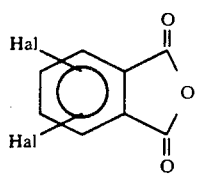

where Hal is F, Cl, Br, or I with water and an alkali metal compound selected from the group consisting of KF, CsF, and $K_2CO_3$, the latter being preferred. The proportions of reactants may vary considerably, however, it is recommended that the alkali metal compound be employed in sufficient proportions to provide at least two equivalents of potassium (or cesium) per mole of dihalophthalic anhydride. Preferably, the alkali metal compound is employed in substantial stoichiometric excess.

Water is a limiting reactant and ideally, for maximum efficiency, is preferably present in a molar proportion of $H_2O$:dihalophthalic anhydride of about 1.0. The water may be added to the initial reaction mixture or alternatively, may be generated in situ. For example, when potassium carbonate is employed in the reaction mixture, a trace amount of water may be present in the initial reaction mixture and additional water generated in situ as the reaction proceeds.

The process of the invention is preferably carried out at atmospheric pressure, but super-atmospheric pressure, for example under autogenous conditions may be employed, if desired.

The process is preferably carried out neat. However, a solvent may be employed. The preferred solvents are polar, aprotic solvents such as N-methyl pyrrolidone, dimethyl formamide, dimethyl acetamide, triglyme, sulfolane, or the like; the most preferred solvent being sulfolane.

The temperature at which the process is carried out may vary considerably, but will generally be within the range of about 120° to about 230° C. Higher or lower temperatures may be employed, but are less preferred. If a solvent is employed, the choice of the solvent may govern the temperature employed. For example, at atmospheric conditions the boiling point of the solvent may become a limiting condition.

In the process, the halogen atoms on the dihalophthalic anhydride reactant function as leaving groups and become the site for the formation of an ether bridge. If the process is carried to completion, two ether bridges will be formed and the product will be dioxydiphthalic anhydride. If the process is stopped after a first ether bridge is formed, the product will be an oxydiphthalic anhydride with the remaining halogen atom(s) as substituents thereon. Thus, when the reactant is a 4,5-dihalophthalic anhydride such as

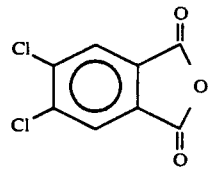

the reaction products will include 4,4'-oxy-5,5'-dihalophthalic anhydride, characterized on the formula

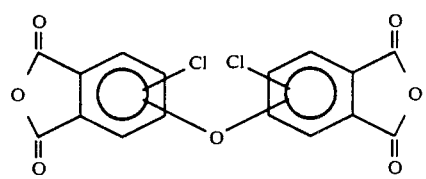

and 4,5,4',5'-dioxydiphthalic anhydride characterized by the formula

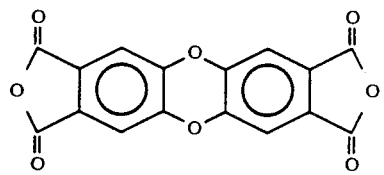

The particular halogen atoms at the 5 and 5'positions will depend on the halogen atoms present at the 5 position of the starting dihalophthalic anhydride. Thus, for example, the above oxydichlorodiphthalic anhydride may be formed from 4,5-dichlorophthalic anhydride starting material. When difluorophthalic anhydride is employed, the corresponding oxydifluoro-diphthalic anhydride may be formed. In addition, a monochloro-oxydiphthalic anhydride may be formed by using as a starting reactant a mixture of a monohalophthalic anhydride, such as 4-chlorophthalic anhydride and a dihalophthalic anhydride, such as 4,5-dichlorophthalic anhydride. Furthermore, the ring site of the oxygen bridge(s) as well as the ring site of the halogen on the dianhydride produced, may be varied by selective choice of the halophthalic anhydride reactant employed. The oxy-dihalo-diphthalic anhydride is formed as an intermediate during the initial stages of reaction. The percentage yield thereof may be enhanced by limiting the time of reaction. Alternatively, by increasing the reaction time, the dioxydiphthalic anhydride is produced as essentially the sole product. The halo-substituted oxydiphthalic anhydride is separable from the dioxydiphthalic anhydride by common physical separation means, such as selective recrystallization, etc. Among the halogenated dianhydrides that may be prepared and employed in the preparation of the polyimides of this invention are those exemplified by the following:

5,5'-dichloro-4,4'-oxydiphthalic anhydride characterized by the formula

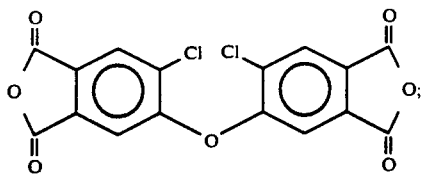

5,5'-difluoro-4,4'-oxydiphthalic anhydride characterized by the formula

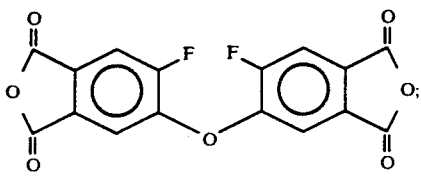

5-chloro-5'-fluoro-4,4'-oxydiphthalic anhydride characterized by the formula

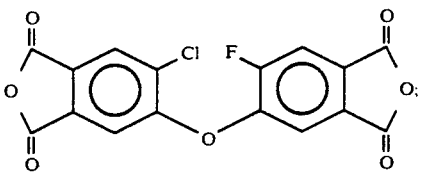

5-chloro-4,4'-oxydiphthalic anhydride characterized by the formula

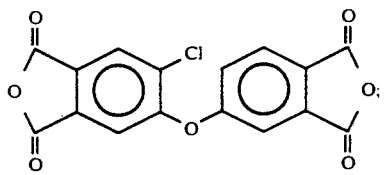

5-fluoro-4,4'-oxydiphthalic anhydride characterized by the formula

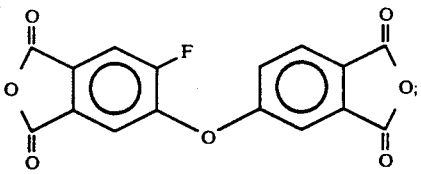

and the like. Bromo- and/or chloro-substituted dianhydrides may be employed to enhance the fire retardant properties of polyimides prepared therefrom. Fluoro-substituted dianhydrides, prepared for example from difluoro-phthalic anhydride, may be employed to improve electrical properties, such as dielectric strength of polyimides. In addition, the presence of fluorine ring substituents should increase the solubility of the polyimide in common solvents.

The dianhydride reactant may include, in addition to the halogenated oxydiphthalics shown above, one or more other dianhydrides, judiciously selected to modify the properties of the final polymer. Among the dianhydrides suitable for use as co-monomers in the polyimides of this invention are Pyromellitic anhydride
Oxydiphthalic anhydride
Dioxydiphthalic anhydride
Bisphenol S dianhydride
Thiodiphthalic anhydride
Biphenyldianhydride
Benzophenone tetracarboxylic dianhydride
Sulfonyl tetracarboxylic dianhydride
Resorcinol bisether dianhydride
Hydroquinone bisether dianhydride
Bisphenol A dianhydride 5,5'-[2,2,2-trifluoro-1-(trifluoromethyl)ethylidene]bis-1,3-isobenzofurandione The preferred dianhydride co-monomers are 4,4'-oxydiphthalic anhydride characterized by the formula

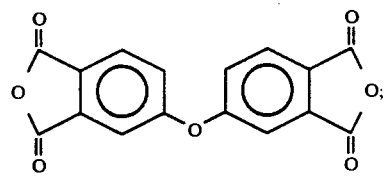

and 4,4',5,5'-dioxydiphthalic anhydride characterized by the formula

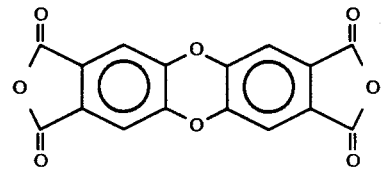

Preferably such dianhydride co-monomers are employed in amounts of less than 80 mole percent of the total dianhydride component.

The polymers and copolymers of the present invention can be prepared by various polymerization methods. One such method is solution polymerization in an essentially anhydrous organic solvent such as dimethylacetamide, N-methylpyrrolidone, dimethylformamide, dichlorobenzene, orthochlorophenol, and the like. The procedure may be carried out by mixing the reactants, that is the diamine and dianhydride(s), in substantially equimolar amounts in the solvent and stirring the reaction mixture for a period of time necessary to allow the reaction to take place. The resultant polyamic acid solution may then be poured onto a suitable substrate such as a glass plate, and the solvent removed by evaporation. The coating may then be heated, for example in a programmable oven, to a temperature in the range of 300°-350° C. to imidize the polyamic acid.

Alternately, chemical imidization may be accomplished using methods such as that described by M.L. Wallach [Journal of Polymer Science, Part A-2; Volume 6, 953-960 (1968)]. In this method the polyamic acid is heated with a mixture of an acid anhydride, such as acetic anhydride, a tertiary amine, such as pyridine, as a base catalyst. Wallach states that this method should yield a polyimide film which is of essentially the same molecular weight of the polyamic acid. Other chemical imidization methods may also be used.

The polyimides of this invention exhibit advantageous properties compared to polyimides derived from unsubstituted oxydiphthalic anhydrides. For example, the polyimides of this invention have improved electrical properties over those derived form the non-halogenated oxydiphthalic anhydrides and, as a result, are better suited for use as insulating materials; for example, as protective coatings on electrical or electronic components. Such coatings may be formed by mixing and reacting the dianhydride(s) and diamines, coating the electrical or electronic component with the resultant polyamic acid and curing, or imidizing the polyamic acid in place. The low dielectric constant of the present polyimides allows the electronic components coated therewith to be placed closer together. The preferred dianhydrides for such applications are the mono- and di-fluorooxydiphthalic anhydrides, used in combination with one or more fluorinated diamines such as oxy-3,3'-bis(5-trifluoromethylbenzamine) or 3,5-diaminobenzotrifluoride.

In addition, the polyimides of this invention exhibit advantageous mechanical properties. For example, the glass transition temperatures of the polymers derived from the halooxydiphthalic anhydrides are lower than those of oxydiphthalic anhydride. This property makes the polyimides of this invention more easily processible than the polyimides from unsubstituted oxydiphthalic anhydrides. The polyimides of this invention also have a higher oxygen index and are therefore less flammable. They also have a higher modulus and greater tensile strength.

The following examples are provided to further illustrate the invention in the manner in which it may be carried out. It will be understood, however, that the specific details given in the examples have been chosen for the purposes of illustration only and are not to be construed as limiting the invention. In the examples, unless otherwise indicated, all parts and percentages are by weight and all temperatures are in degrees Celsius.

EXAMPLES 1 and 2

Preparation of Halo-oxydiphthalic Anhydrides

Example 1

Potassium fluoride (5.04 g) and Carbowax MPEG 2000 (0.71 g) were added to and mixed with 10.2 g of a mixture of 56.1% (GC area percent) 4,5-difluorophthalic anhydride and 43.9% (GC area percent) 4-chloro-5-fluorophthalic anhydride. The powdery mixture was heated in a flask to 180° C., forming a viscous, paste-like reaction mixture. The temperature was maintained at 180°-207° C. for approximately 3.5 hours, during which a portion of the reaction mixture sublimed and condensed on the upper portion of the flask. The flask was cooled to room temperature and the sublimate collected (6.69 g) and analyzed by gas chromatography, indicating, in area percent, 74% 4,5-difluorophthalic anhydride and 26% 4-chloro-5-fluorophthalic anhydride. The reaction mixture remaining at the bottom of the flask (7.58 g) was analyzed by gas chromatography and found to contain in area percent, 50.1% 4,5-difluorophthalic anhydride; 42.8% 4-chloro-5-fluorophthalic anhydride; 3.4% 4,4'-difluoro-5,5'-oxydiphthalic anhydride, 2.1% 4-chloro-4'-fluoro-5,5'-oxydiphthalic anhydride; 0.3% 4,4'-dichloro-5,5'-oxydiphthalic anhydride and 1.0% 4,4',5,5'-dioxydiphthalic anhydride.

Example 2

A solution of equal molar amounts of 4-chlorophthalic anhydride (18.2 g, 0.1 mole) and 4,5-dichlorophthalic anhydride (21.7 g, 0.1 mole) in 60 g of sulfolane is heated to 180°-210° C. Temperature is maintained, with stirring, while 0.05 mole (6.91 g) of potassium carbonate is added over a period of about one hour. The temperature is maintained for an additional two hours, then lowered to room temperature, to yield a mixture of 5-chloro-4,4'-oxydiphthalic anhydride; 5,5'-dichloro-4,4'-oxydiphthalic anhydride; and 4,4',5,5'-dioxydiphthalic anhydride.

EXAMPLES 3 to 5

Preparation of Polyimides

Example 3

4,4'-Oxydianiline (50 mg, 2.5 mmol) is dissolved in 7.4 g of N,N-dimethylacetamide (DMAc). 5,5'-Oxybis(6,6'-difluoro-1,3-isobenzofurandione) (86.5 mg, 2.5 mmol), is added and the mixture stirred overnight to yield a clear, thick solution of the polyamic acid. The polyamic acid solution is coated on a soda-lime glass plate and placed in a drying chamber with dry nitrogen passing through it to remove most of the DMAc. The plate is transferred to an oven with a heatin9 program of 100° C. for one hour followed by one hour each at 200° and 300° C.

Example 4

4,4'-Oxydianiline (50 mg, 2.5 mmol) is dissolved in 7.4 g of N,N-dimethylacetamide (DMAc). 4,4'-Oxydiphthalic anhydride (194 mg, 0.625 mmol) and 5,5'-oxybis(6,6'-difluoro-1,3-isobenzofurandione) (631.5 mg, 1.825 mmol), is added and the mixture stirred overnight to yield a clear, thick solution of the polyamic acid. The polyamic acid solution is coated on a soda-lime glass plate and placed in a drying chamber with dry nitrogen passing through it to remove most of the DMAc. The plate is transferred to an oven with a heating program of 100° C. for one hour followed by one hour each at 200° and 300° C.

Example 5

4,4'-Oxydianiline (50 mg, 2.5 mmol) is dissolved in N,N-dimethylacetamide (DMAc, 7.4 g). 5,5'-Oxybis(6,6'-dichloro-1,3-isobenzofurandione) (947 mg, 2.5 mmol), is added and the mixture stirred overnight to yield a clear, thick solution of the polyamic acid. The polyamic acid solution is coated on a soda-lime glass plate and placed in a drying chamber with dry nitrogen passing through it to remove most of the DMAc. The plate is transferred to an oven with a heating program of 100° C. for on hour followed by one hour each at 200° and 300° C.

What is claimed is:

1. A polyimide comprising recurring imide structural units of the formula

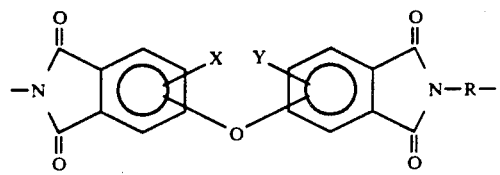

where X is F, Cl, Br, or I; Y is H, F, Cl, Br, or I; and R is a divalent organic radical.

2. A polyimide according to claim 1 wherein R is a divalent organic radical selected from the group consisting of (a) aromatic hydrocarbon radicals or halo- or halomethyl-substituted aromatic hydrocarbon radicals of 6 to 20 carbon atoms, (b) alkylene radicals and cycloalkylene radicals having from 2 to about 20 carbon atoms, $C_{2-8}$) alkylene terminated polydiorganosiloxanes, and (c) divalent radicals included within the formula

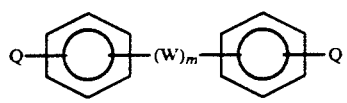

where Q is S, $SO_2$, O, or a direct bond; m is 0 or 1; and W is a member selected from the class consisting of divalent radicals of the formulas,

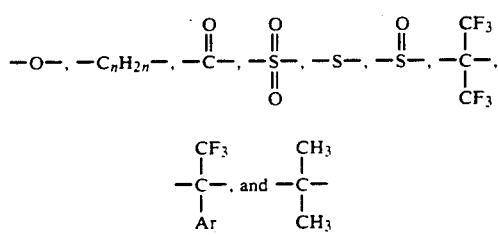

where n is a whole number from 1 to 5, and Ar is an aromatic hydrocarbon or halogen or halomethyl substituted aromatic hydrocarbon of 6 to 20 carbon atoms.

3. A polyimide according to claim 1 wherein R is

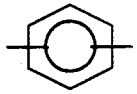

4. A polyimide comprising the condensation product of substantially equimolar amounts of
A) at least one dianhydride reactant comprising a halo-oxydiphthalic anhydride of the formula

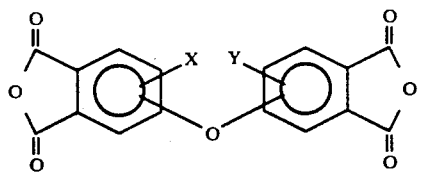

where X is F, Cl, Br or I, and Y is H, F, Cl, Br or I; and
B) at least one diamine of the formula $NH_2RNH_2$ where R is a divalent organic radical selected from the group consisting of (a) aromatic hydrocarbon radicals having from 6 to about 20 carbon atoms and halogenated derivatives thereof, (b) alkylene radicals and cycloalkylene radicals having from 2 to about 20 carbon atoms, $C_{2-8}$) alkylene terminated polydiorganosiloxanes, and (c) divalent radicals included within the formula

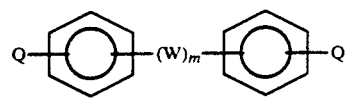

where Q is S, O, $SO_2$, or a direct bond; m is 0 or 1; and W is a member selected from the class consisting of divalent radicals of the formulas

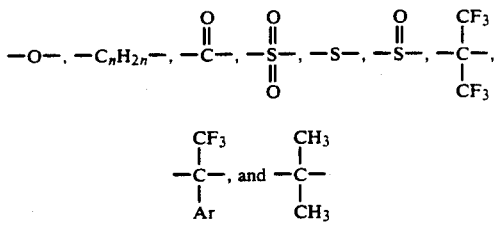

where n is a whole number from 1 to 5, and Ar is an aromatic hydrocarbon or halogen or halomethyl substituted aromatic hydrocarbon of 6 to 20 carbon atoms.

5. A polyimide according to claim 4 wherein the dianhydride is a dihalo-oxydiphthalic anhydride of the formula

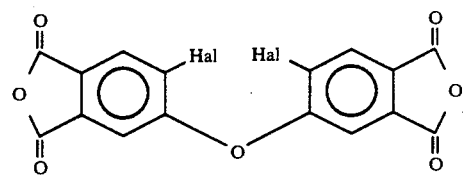

where each Hal is independently Cl, F, or Br.

6. A polyimide according to claim 5 wherein the diamine is 4,4-oxy-dianiline.

7. A polyimide according to claim 6 wherein the dianhydride is a difluoro-oxydiphthalic anhydride of the formula

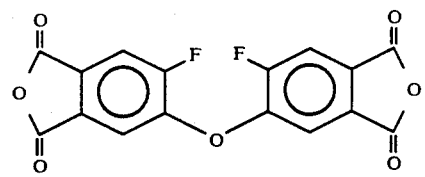

8. A polyimide according to claim 6 wherein the dianhydride is a dichloro-oxydiphthalic anhydride of the formula

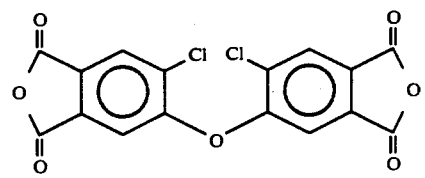

* * * * *